US008445581B2

(12) United States Patent
Gunatillake et al.

(10) Patent No.: US 8,445,581 B2
(45) Date of Patent: May 21, 2013

(54) BIOCOMPATIBLE POLYMER COMPOSITIONS

(75) Inventors: Pathiraja Arachchillage Gunatillake, Mulgrave (AU); Roshan Tyrrel Anton Mayadunne, Wheelers Hill (AU); Raju Adhikari, Glen Waverely (AU); Heng Chy Taing, Chadstone (AU); Tam Phuong Thi Le, Clematis (AU); Jerome Anthony Werkmeister, Camberwell (AU); John Alan Maurice Ramshaw, Pascoe Vale (AU); Jacinta Frances White, Elsternwick (AU); Tracy Ann Tebb, Ballarat (AU)

(73) Assignee: Polynovo Biomaterials Pty Limited, Clayton, Victoria (AU)

( * ) Notice: Subject to any disclaimer, the term of this patent is extended or adjusted under 35 U.S.C. 154(b) by 617 days.

(21) Appl. No.: 12/309,794

(22) PCT Filed: Aug. 2, 2007

(86) PCT No.: PCT/AU2007/001085
§ 371 (c)(1),
(2), (4) Date: Jun. 3, 2009

(87) PCT Pub. No.: WO2008/014561
PCT Pub. Date: Feb. 7, 2008

(65) Prior Publication Data
US 2009/0324675 A1 Dec. 31, 2009

(30) Foreign Application Priority Data

Aug. 2, 2006 (AU) ................................ 2006904181

(51) Int. Cl.
*C08F 290/02* (2006.01)
*C08F 299/00* (2006.01)
*C08G 63/08* (2006.01)
*C08L 33/04* (2006.01)

(52) U.S. Cl.
USPC ........... 524/500; 524/502; 524/503; 524/504; 524/505; 524/513; 524/537; 524/539; 525/56; 525/58; 525/60; 525/61; 525/63; 525/64; 525/67; 525/90; 525/91; 525/92 A; 525/92 E; 525/92 F; 525/92 L; 525/92 R; 525/165; 525/170; 525/185; 525/186; 525/188; 525/410; 525/412; 525/417; 525/437; 525/439; 525/462; 525/468; 525/535; 525/538

(58) Field of Classification Search
USPC ................. 525/56, 58, 60, 61, 63, 64, 67, 90, 525/91, 92 A, 92 E, 92 F, 92 L, 92 R, 165, 525/170, 185, 186, 188, 410, 412, 417, 437, 525/439, 462, 468, 535, 538, 500, 502, 503, 525/504, 505, 513, 537, 539
See application file for complete search history.

(56) References Cited

U.S. PATENT DOCUMENTS

| | | | |
|---|---|---|---|
| 3,007,899 A | 11/1961 | Urs | 528/76 |
| 3,247,282 A | 4/1966 | Englisch | 528/306 |
| 3,281,378 A | 10/1966 | Garber et al. | 260/2.5 |
| 3,360,546 A | 12/1967 | Wygant et al. | 560/191 |
| 4,035,274 A | 7/1977 | McGinniss | 522/9 |
| 4,192,827 A | 3/1980 | Mueller et al. | 525/123 |
| 4,273,690 A | 6/1981 | Walus | 525/7 |
| 4,284,506 A | 8/1981 | Tetenbaum et al. | 210/321.6 |
| 4,293,679 A | 10/1981 | Cogliano | 528/48 |
| 4,412,033 A | 10/1983 | LaBelle et al. | 524/590 |
| 4,424,252 A | 1/1984 | Nativi | 428/209 |
| 4,451,523 A | 5/1984 | Nativi et al. | 428/209 |
| 4,908,406 A | 3/1990 | Mulhaupt et al. | 525/64 |
| 4,935,480 A | 6/1990 | Zdrahala et al. | 528/28 |
| 5,041,516 A | 8/1991 | Frechet et al. | 528/44 |
| 5,109,077 A | 4/1992 | Wick | 525/467 |
| 5,276,068 A | 1/1994 | Waknine | 522/28 |
| 5,578,662 A | 11/1996 | Bennett et al. | 524/54 |
| 5,886,127 A | 3/1999 | Newkome et al. | 528/49 |
| 5,981,684 A | 11/1999 | Bruchmann et al. | 528/45 |
| 6,124,370 A | 9/2000 | Walton et al. | 521/143 |
| 6,150,438 A | 11/2000 | Shiraishi et al. | 524/35 |
| 6,376,637 B1 | 4/2002 | Bruchmann et al. | 528/60 |
| 6,376,742 B1 | 4/2002 | Zdrahala et al. | 623/11.11 |
| 6,388,047 B1 | 5/2002 | Wan et al. | 528/354 |

(Continued)

FOREIGN PATENT DOCUMENTS

| | | |
|---|---|---|
| EP | 837084 | 4/1998 |
| JP | 07-070296 | 3/1995 |

(Continued)

OTHER PUBLICATIONS

Office Action in EP 03 739 861.7, Jan. 18, 2008, Polynovo Biomaterials Pty Ltd.

(Continued)

*Primary Examiner* — Ana Woodward
(74) *Attorney, Agent, or Firm* — Novak Druce Connolly Bove + Quigg LLP

(57) ABSTRACT

The present invention provides a biocompatible prepolymer comprising hydrophilic and hydrophobic segments, wherein the hydrophobic segments have at least one ethylenically unsaturated functional group and at least 5% of the segments have two or more ethylenically unsaturated functional groups and water. The invention further provides a biocompatible prepolymer composition comprising hydrophilic and hydrophobic prepolymers, wherein at least one of the hydrophobic prepolymers has at least one ethylenically unsaturated functional group and at least 5% of the prepolymers have two or more ethylenically unsaturated functional groups and water. The invention further provides use of the prepolymer or prepolymer compositions of the invention in biomedical applications such as tissue engineering, as bone substitutes or scaffolds, and in wound treatment.

14 Claims, 7 Drawing Sheets

U.S. PATENT DOCUMENTS

| | | |
|---|---|---|
| 2001/0005738 A1 | 6/2001 | Bruchmann et al. ............ 525/123 |
| 2002/0103347 A1 | 8/2002 | Isaka et al. .................... 530/413 |
| 2003/0153673 A1 | 8/2003 | Schwalm et al. ............. 524/589 |
| 2004/0097684 A1 | 5/2004 | Bruchmann et al. ............ 528/44 |
| 2005/0112203 A1 | 5/2005 | Shau et al. .................... 424/489 |
| 2006/0074208 A1 | 4/2006 | Laredo .......................... 526/279 |

FOREIGN PATENT DOCUMENTS

| | | |
|---|---|---|
| WO | WO 99/02168 | 1/1999 |
| WO | WO 00/12579 | 3/2000 |
| WO | WO 00/67813 | 11/2000 |
| WO | WO 02/09655 | 2/2002 |
| WO | WO 02/10247 | 2/2002 |
| WO | WO 02/10292 | 2/2002 |
| WO | WO 2004/065450 | 8/2004 |
| WO | WO 2005/089778 | 9/2005 |
| WO | WO 2006/010278 | 2/2006 |

OTHER PUBLICATIONS

Arroyo et al. Revista de Plasticos Modernos, 218:217-226, 1974.
Yoshida et al. Agricultural and Biological Chemistry 34(11):1668-1675.
Ogata et al., Biochemica et Biophysica Acta, 742:384-390, 1983.
STN Database, File Registry, Registry No. 57214-23-0.
STN Database, File CA, Accession No. AN 82:113308.

BIOCOMPATIBLE POLYMER COMPOSITIONS

CROSS REFERENCE TO RELATED APPLICATIONS

The present application is a National Phase Application of International Application No. PCT/AU2007/001085 filed Aug. 2, 2007, which claims priority to Australian Patent Application No. 2006904181 filed Aug. 2, 2006, which applications are incorporated herein fully by this reference.

FIELD

The present invention relates to biocompatible prepolymers and prepolymer compositions. The prepolymer and prepolymer compositions are capable of curing to form cross linked polymer networks in the presence of biological components such as cells and growth factors and can be used in cell delivery and biomedical applications such as tissue engineering, drug delivery, bioadhesives and scaffolds in wound healing, bone substitutes or scaffolds for nerve repair, cements in dental and periodontal applications and anti adhesive or protective barriers.

BACKGROUND OF THE INVENTION

A major hurdle in developing tissue engineered products and therapies is the lack of suitable substrates which can act as cell delivery platforms and form three dimensional scaffolds for cells to grow and to provide the mechanical support during the tissue regeneration process. Such polymer systems could be useful in arthroscopic delivery of cells to repair damaged tissues in the body. These cell delivery systems allow the exploitation of the full potential of tissue engineering field and assist the body to repair its damaged tissues and organs. Despite many recent advances in the design and development of suitable polymers for fabricating scaffolds, the existing polymer systems do not meet the demanding criteria for cell delivery.

Several criteria must be achieved if such a polymer system is to be useful for cell delivery. It must be non cytotoxic before and after curing and provoke no inflammatory response in the body. The method of the initiation of polymerisation to form the polymer network should be tolerant to the cells and other components used. The polymer network formed should have sufficient porosity to facilitate cell-polymer interactions, and to allow the transport of nutrients to the cells, and also provide sufficient space for the growth of the extra cellular matrix. A polymer system that can be tailored to have different mechanical properties depending on the type of tissues to be regenerated will have advantages in regenerating different types of biological tissues. For example, a system that sets to a high modulus material would be useful in orthopaedic applications. Furthermore, the viscosity of the polymer/cell mixture should be such that it can be delivered using a syringe or an arthroscopic method. This provides substantial advantages in employing minimally invasive surgical techniques to be used in treatments to repair damaged body tissues such as fractured bones, damaged knee cartilages, or other body tissues and organs.

Natural polymers such as alginate, fibrin, argrose, collagen, methylcellulose, hyluronon and peptide-based hydrogels have been investigated as cell delivery systems with some success. Primarily due to the ability of such polymers to accommodate large quantities of water and their good biocompatibility, cells stay viable in those systems. Accordingly, formulations based on natural polymers have been developed primarily as cell encapsulation products. The formation of a gel from these polymers is achieved by exploring the thermo reversible characteristics of some of the polymers or the use of ionic strength to transform to a gel in some cases. These properties of natural and some synthetic polymers have been explored as cell encapsulation systems.

Chemical modification to introduce cross linkable functional groups has also been investigated. A major draw back of such polymer systems is the very poor mechanical strengths of the cross linked hydrogel. While these systems are useful as cell-encapsulation systems, their utility in tissue engineered products and therapies are limited, particularly when high mechanical strength of the gel is required.

Likewise, synthetic polymers have been investigated for preparing hydrogels for cell encapsulation/delivery purposes. Hydrophilic polymers such as poly(ethylene) glycol, end functionalized with acrylates have been investigated for cell encapsulation. The gels formed by cross linking are generally mechanically very weak, not too different to those based on natural polymers. Although synthetic polymers may provide the best option to develop systems with appropriate mechanical strength, synthetic polymer systems reported to date do not provide adequate mechanical properties nor do they have the ability to incorporate cells without affecting their viability.

Repair and regeneration of load-bearing tissues such as cartilage and bone require the cell delivery polymer system to have sufficient mechanical strength over a considerable period of time for the tissue regeneration to be complete. Ideally the mechanical strength should be comparable to that of the type of tissue to be repaired or regenerated. A mechanically inferior gel would most likely disintegrate due to compressive, torsional or tensile forces such tissues are subjected to well before the defect site is repaired. The gels based on natural polymers and synthetic polymers in general do not provide sufficient mechanical support in such situations. Accordingly, there is a need for cell delivery polymer systems which can be tailored to have sufficient mechanical strength depending of the type of tissue to be repaired/regenerated. It is also a requirement that the gels maintain cell friendly environment before and after cross linking the polymer. Ideally, the polymer should degrade and the degradation products be completely released from the body once the damage is repaired.

SUMMARY

The invention relates to biocompatible prepolymers that can accommodate biological components such as cells and growth factors and provide an environment for cells to retain viability over sufficiently long periods of time to allow the delivery of the prepolymer to a defect site. The prepolymers are suitable for delivery using injection or arthroscopic type means and can be cross linked by radiation or other methods without harming the cells or other components present in the composition. The invention also relates to cured polymeric end products that retain biocompatibility and provide adequate mechanical strength for the cells to migrate, propagate and rebuild the biological tissue structure.

According to the present invention there is provided a biocompatible prepolymer comprising:
hydrophilic and hydrophobic segments, wherein the hydrophobic segments have at least one ethylenically unsaturated functional group and at least 5% of the segments have two or more ethylenically unsaturated functional groups; and water.

There is also provided a biocompatible prepolymer composition comprising:

hydrophilic and hydrophobic prepolymers, wherein at least one of the hydrophobic prepolymers has at least one ethylenically unsaturated functional group and at least 5% of the prepolymers have two or more ethylenically unsaturated functional groups; and water.

Further according to the present invention there is provided a biocompatible polymer composition which is the reaction product of:
hydrophilic and hydrophobic prepolymers, wherein at least one hydrophobic prepolymer has at least one ethylenically unsaturated functional group and at least 5% of the prepolymers have two or more ethylenically unsaturated functional groups; and water.

The term "ethylenically unsaturated functional group" refers to functional groups containing double or triple bonds joined by two carbon atoms such as acrylates, methacrylates, allylic groups which are capable of undergoing free radical polymerisation.

Some of the hydrophobic prepolymers are novel and form another aspect of the invention. Thus, the present invention also provides a hydrophobic (co)polyol comprising a plurality of substituents containing repeat units derived from an α-hydroxy acid pendant from and chemically bonded to a core molecule.

In a preferred embodiment the hydrophobic (co)polyol is prepared by polymerisation of a core molecule and a hydroxy acid.

The prepolymers are soluble, miscible or form an emulsion or paste when mixed with water. As the prepolymers are biocompatible they can be combined with cells, growth factors and other biological or non-biological components and the appropriate cell culture media to provide nutrients for cells to retain viability and proliferate to grow tissue and associated extracellular matrix. The cells retain their viability in the prepolymers and are not harmed by the chemical and physical changes associated with the curing process employed to convert the prepolymers to a cross linked polymer network. At least one initiator may be added to the prepolymer or prepolymer composition to initiate polymerisation and convert the prepolymer to a cross linked network.

The invention further provides a cured biocompatible polymer comprising the reaction product of the prepolymer or prepolymer composition defined above and at least one initiator.

The invention still further provides a biocompatible scaffold comprising the reaction product of the prepolymer or prepolymer composition defined above and at least one initiator.

There is also provided use of the prepolymer or prepolymer composition defined above and at least one initiator as a biocompatible scaffold for tissue engineering applications, such as wound treatment and bone, cartilage and nerve repair.

There is further provided a method of treating wounds and damaged bone, cartilage or nerves in a subject in need thereof comprising either:
implanting a scaffold prepared ex vivo from the cured biocompatible polymer defined above; or
injecting the prepolymer or prepolymer composition defined above and at least one initiator in uncured form for in vivo curing and scaffold preparation.

DETAILED DESCRIPTION

The present invention relates to biocompatible prepolymers having hydrophilic and hydrophobic segments and ethylenically unsaturated functional groups and biocompatible prepolymer compositions containing at least one hydrophilic prepolymer and at least one hydrophobic prepolymer. The prepolymers and prepolymer compositions are water miscible, soluble or form emulsions when mixed with water.

The invention also relates to cured biocompatible polymers which may be used as scaffolds for tissue engineering applications prepared by reacting the prepolymers or prepolymer compositions with at least one initiator to form a cross-linked network.

The term "biocompatible" includes histocompatible and refers to a compatibility when in contact with cells and/or bodily fluids of living animals or humans.

Hydrophobic/Hydrophilic Prepolymers

The term "prepolymer" refers to a polymer which is yet to be cured in a curing stage.

The term "hydrophobic prepolymer" refers to a prepolymer which has segments/functional groups which render the prepolymer water insoluble or immiscible and unable to make emulsions with water on its own.

The term "hydrophilic prepolymer" refers to a prepolymer which has segments/functional groups which enable the prepolymer to be water soluble, miscible or capable of forming an emulsion or paste when mixed with water.

The hydrophobic prepolymers preferably comprise segments derived from hydrophobic polyols and may be regularly branched such as a star polymer or dendritic or irregularly branched such as hyperbranched. The hydrophobic prepolymer preferably has at least two ethylenically unsaturated functional groups and at least one other functional group such as hydroxyl, thiol, amine or carboxyl for reaction with the isocyanate group of the hydrophilic prepolymer.

The hydrophilic prepolymer is preferably prepared from hydrophilic linear polyols and a diisocyanate such that the prepolymer has at least one isocyanate functional group for reaction with the hydrophobic prepolymer. The relative proportions of the hydrophilic and hydrophobic segments in the prepolymer are chosen such that the prepolymer is soluble, miscible or forms an emulsion or paste when mixed with water.

If desired the hydrophilic and hydrophobic prepolymers may be formulated by reversing the hydrophilic and hydrophobic order. For example, the star/dendritic/hyperbranched prepolymer can be prepared using the hydrophilic polyols and the urethane-based linear prepolymer can be prepared using hydrophobic polyols.

The term "polyol" refers to a molecule which has at least two or more functional hydroxyl groups that can react with isocyanate groups to form urethane groups. Examples of polyols include but are not limited to diols, triols, and macromers such as macrodiols. Preferably the polyol has a molecular weight of 300 to 10000, more preferably 300 to 5000, and even more preferably 300 to 2000. It will be understood that the molecular weight values referred to herein are "number average molecular weights". Oligomers with two or more hydroxyl, thiol, amine and carboxyl groups or any combination of those can be used to prepare the prepolymers according to the invention.

Suitable hydrophobic polyols include tri or higher hydroxy or amine functionalised oligomers based on polyesters, polyethers, polycarbonates, polysiloxanes, polyanhydrides, polyorthoesters, polylactones, polyimides and polyphosphazenes.

Suitable hydrophilic polyols include polyethylene glycol, polypropylene glycol, polyvinyl alcohol and polythiols based on butanedithiol, hexanedithiol or pentaerythritol tetrakis (3-mercaptopropionate) or copolymers thereof.

Preferred structures of the prepolymers of the present invention are represented by the general formulae (I) and (II) below.

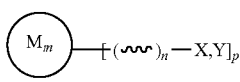

in which
ᨆ represents a repeat unit derived from an α-hydroxy acid, a dihydroxy compound, dicarboxylic acid, diols or mixtures thereof;
M is a core molecule;
m is the number of hydroxyl groups in the core molecule;
n is an integer from 1 to 50;
p is the number of arms containing repeat units bonded to the core molecule; and
X and Y are independently functional groups such as acrylate or hydroxyl.

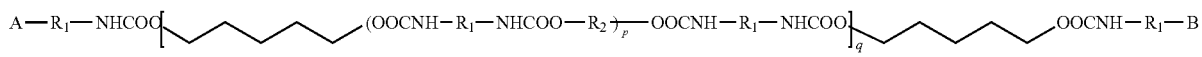

in which
A and B are independently functional groups such as NCO, hydroxyl, amine $C_{1-10}$ alkyl or aryl;
$R_1$ and $R_2$ are independently selected from $C_{1-18}$ alkylene or arylene groups;
p is 0 to 10; and
q is 1 to 50.

Examples of α-hydroxy acids include glycolic acid, lactic acid, DL-lactic acid, L-lactic acid, D-lactic acid, hydroxy propionic acid, hydroxy butyric acid, mandelic acid and caproic acid. The hydroxy compounds may include 1,2-ethanediol, 1-3-propanediol 1,4-butanediol and 1,6-hexanediol.

The term "core molecule" refers to a molecule which has at least two and preferably three or more functional groups that can react with isocyanate groups to form urethane or urea groups. Preferably the core molecule has a molecular weight of 400 or less. Examples of core molecules include but are not limited to diols, triols and polyols such as sugar molecules.

Examples of core molecules are as follows:
1. Pentaerythritol
2. Glycerol
3. Dipentaerythritol
4. Tripentaerythritol
5. 1,2,4-Butanetriol
6. Trimethylolpropane
7. 1,2,3-Trihydroxyhexane
8. Myo-inositol
9. Ascorbic acid
10. Glucose and isomers such as D-galactose and D-mannose, D-fructose
11. Maltose
12. Sucrose
13. Mannitol
14. N-Acetyl-D-glucosamine
15. Butane trithiols
16. Pentaerythritol tetrakis such as mercaptopropionate
17. Diethanolamine
18. Diisopropanolamine
19. Tris(hydroxymethyl)aminomethane.

The terms "$C_{1-18}$ alkylene" and "arylene" are the divalent radical equivalent of the terms "$C_{1-18}$ alkyl" and "aryl", respectively. The two bonds connecting the alkylene or aryl to the adjacent groups may come from the same carbon atom or different carbon atoms in the divalent radical.

The terms "$C_{1-10}$ alkyl" or "$C_{1-18}$ alkyl" refer to linear, branched or cyclic hydrocarbon groups having from 1 to 10 or 1 to 18 carbon atoms. Illustrative of such alkyl groups are methyl, ethyl, propyl, isopropyl, butyl, sec-butyl, tert-butyl, pentyl, neopentyl, hexyl, cyclopropyl, cyclobutyl, cyclopentyl or cyclohexyl.

The term "aryl" refers to a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

Preferred prepolymers of the present invention are reaction products of (I) and (II), a combination of (I) and (II) such as a blend, or polyol (I) when both hydrophilic and hydrophobic segments are present as block, random or alternating copolymers and at least two of the hydroxyl groups are reacted to form ethylenically unsaturated groups.

For example, to prepare a prepolymer which is a reaction product of the two prepolymers, prepolymer (I) is chosen with repeat units having hydrophobic properties, acrylate end functional groups and at least one hydroxy group per prepolymer molecule. The prepolymer is then reacted with (II) which has hydrophilic segments and isocyanate end groups. The resulting reaction product has both hydrophilic and hydrophobic segments.

Similarly, the two prepolymers (I) and (II) could be functionalised to have acrylate functional groups and no functional groups that can react with each other such that there is no chemical reaction between the two when combined to form an emulsion.

Further, the polyol (I) may be chosen to have both hydrophobic and hydrophilic segments. Examples of such polyols include copolymer star polyols based on ethylene glycol with either lactic acid, glycolic acid, caproic acid or mixtures thereof. Star polyols with polyethylene glycol blocks within the inner core and polylactic acid outer structure are commercially available (Polymer Source™) These polyols can also be prepared according to literature reported procedures using anionic living polymerisation of ethylene oxide, followed by condensation or cationic polymerisation of lactide.[1]

Commercially available polyols can be used to prepare prepolymers according to the present invention. For example, polycaprolactone triol (PCLT) may be reacted with isocyanato ethyl methacrylate (IEM) to convert on the average two hydroxyl end groups of PCLT to methacrylate end groups. The remaining hydroxyl group is available for reaction with (II). The prepolymer (II) may be prepared by reacting a hydrophilic polyol such as poly(ethylene glycol) and a diisocyanate such as ethyl lysine diisocyanate to have a prepolymer with isocyanate end functional groups. Reacting two molar equivalents of (II) with one molar equivalent of (I) will produce a prepolymer that is biocompatible, can take up a high proportion of water and forms a stable suspension of live cells when mixed with cells and nutrient solution. A representative example of a prepolymer of this type is as follows:

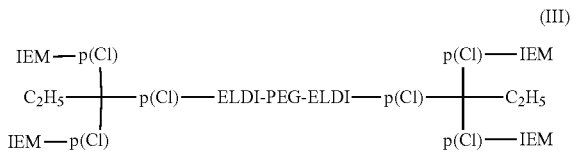

(III)

The present invention also provides new hydrophobic (co) polyols which are prepared by polymerisation, preferably condensation polymerisation, of a core molecule such as pentaerythritol, glycerol or glucose and a hydroxy acid such as lactic acid, glycolic acid, mandelic acid or a hydroxy aromatic acid for example salicylic acid or terepthalic acid.

The condensation polymerisation can optionally be carried out in the presence of a catalyst such as stannous 2-ethylhexanoate. This process provides colourless polyols with molecular weights in the range of 120 to 30,000 K, low acid numbers, narrow polydispersity and quantitative yield. Polyols with end groups such as primary and secondary hydroxyl groups and thiols can be obtained. The polymerisation requires relatively short reaction times. Other methods such as ring-opening polymerisation of the corresponding cyclic monomers of hydroxy acids can also be used to prepare the hydrophobic polyols.

Hydrophilic prepolymers can also be prepared using known hydrophilic prepolymers such as polyvinyl alcohol, polyacrylamides, polyvinyl pyrolidone and polyhydroxyethyl methacrylate or block, graft or random copolymers thereof. For example, the hydroxy groups of polyvinyl alcohol can be functionalised with isocyanate ethyl methacrylate to provide ethylenically unsaturated groups so that a cross linked polymer network is formed when the acrylate functionalised polyvinyl alcohol is combined with a hydrophobic prepolymer and cured.

The preferred diisocyanates used to prepare prepolymer (II) include aliphatic diisocyanates such as 1,4-hexamethylene diisocyanate, 1,4 butanediisocyanate, ethyl lysine diisocyanate (ELDI), methyl lysine diisocyanate, isophorone diisocyanate and 2,2,4-trimethyl hexamethylene diisocyanate. Isothiocyanates such as butanediisothiocyanate, hexamethylene diisothiocyanate, xylene diisothiocyanate and dicyclohexylmethane diisothiocyante can also be used.

The use of a conventional chain extender ($R_2$ in formula (II)) is optional in preparing prepolymer (II). Preferred chain extenders include $C_{2-10}$ alkylene glycols such as ethylene glycol and propylene glycol; $C_{2-10}$ alkane diols such as butane diol and propanediol; amines such as ethanol amines, ethylenediamine, propanediamine and butane diamine; and chain extenders having one or more hydrolysable (degradable) functional groups in the backbone such as those described in Australian Patent Application No. 2005905792.

The preferred molecular weight of prepolymer (I) is in the range 300 to 10000, more preferably 300 to 5000, most preferably 300 to 2000. The preferred molecular weight of prepolymer (II) is in the range 500 to 50000, more preferably in the range is 500 to 5000, most preferably 500 to 2000.

It will be appreciated that the molecular weight of the two prepolymers (i) and (II) and the relative proportions influence the mechanical properties of the cross linked polymer network. The amount of water that can be incorporated is largely governed by the proportion of the hydrophilic prepolymers in the composition.

Dispersants or Porogens

The compositions of the invention may also contain dispersants including biological components such as cells for example osteoblasts, chondrocytes, fibroblasts, melanocyts and endothelial cells and growth factors; bioactive molecules such as biopharmaceuticals, natural polymers for example alginate, fibrin, argrose, collagen, methylcellulose and peptide-based hydrogels and drugs; other components for supporting cell growth such as nanoparticulate hydroxyapatite, calcium phosphate and hydroxyapatitle; adhesives such as fibrin, collagen and transglutaminase systems; surfactants such as siloxane surfactants; silica particles, powdered silica; hollow fibres which may be used to seed cells; or porogens such as water and gelatin beads.

The prepolymers and prepolymer compositions are particularly useful for combining with cells, media with nutrients or growth factors as well as other cell friendly additives such as hydroxyapatite and tricalcium phosphate. These compositions after injecting or delivering to a defect site can be cured (cross linked) inside the body or may be cured outside the body and cultured to form tissue layers, whole or parts of organs. The cells may be encapsulated using well known methods and incorporated with the prepolymers. Cells cultured on beads such as gelatin and deminaralized bone may be incorporated with the prepolymers.

The invention also enables the preparation of prepolymers capable of holding different amounts of water. Compositions with relatively large amounts of water such as at least 60 wt %, preferably 70 wt % more preferably 85 wt % can be prepared for the delivery of cells. In these compositions, the water forms channels and these channels allow the flow of nutrients to the cells and also facilitate the removal of any waste products.

By formulating prepolymer compositions to hold different amounts of water, polymers with mechanical properties to match those of different body tissues can be prepared. For example, polymers to match mechanical properties of cartilage can be formulated. Such compositions are particularly suited for delivery of chondrocytes to help repair damaged articular cartilage. Likewise, more rigid polymers could be prepared by choosing the appropriate hydrophobic components and the amount of hydrophilic components and also by adjusting the water uptake and such polymers are particularly suited for delivery of osteoblasts for fracture fixation or fixing other bone defects. Similarly, polymers with properties to match the human skin are suited to deliver cells such as fibroblasts, melanocytes and endothelial cells to repair wounds.

Initiator

The term "initiator" refers to at least one molecule which when activated by an energy source, will result in free radical polymerisation of the prepolymers in a curing step. The energy source initiating the polymerisation may be thermal, photolytic or based on a redox system of components with the result that free radical polymerisation occurs to cure the prepolymer composition.

The selection of the initiator present in the prepolymer composition for the purpose of triggering free radical curing is dependant on the method of initiation selected. Initiation may be thermal, photolytic or based on a redox system of components and is preferably by an external source. For example, camphorquinone, phosphine oxide based initiators such as 2,4,6-trimethyl benzoyl) diphenyl phosphine oxide are suitable and redox initiators such as ammonium persulfate and sodium metabisulfite, gamma radiation or laser are also suitable. For in-vivo applications photolytic initiators or redox based systems are preferred. More preferable is a system that cures the polymeric composition using a wave length that is either in the UV or visible region of electromagnetic radiation. Of the two, visible light initiation is more desirable in biomedical applications. In one embodiment of the invention, visible light source having a maximum wave length of 450±30 nm is used. Examples of photoinitiators include but are not limited to 2,2-dimethoxy-2-phenylacetophenone (Irgacure 651), hydroxyalkyl phenones (1-hydroxycyclohexyl phenyl ketone (Irgacure 184), 2-methyl-1-[4-(methylthio) phenyl]-2-(4-morpholinyl)-1-propanone (Irgacure 907), 2-hydroxy-1-[4-(hydroxyethoxy)phenyl]-2-methyl-1-propanone (Darocur 2959), Darocur 4265, Darocur TPO, Darocur 1173, Irgacure 500, 784, 907, 2959, 819, 2020, 1000, 369, 651, 1300, 819/819W, Irgacure 2005 and Irgacure 2010W and Irgacure 2020, polysilanes, Esacure KP150 (Hydroxyalkylphenylketone), Camphorquinone, Rosebengal, ethyl-4-N,N-dimethylamino-benzoate (4EDMAB)/triethanolamine, α alkoxydeoxy-benzoins, α,α-dialkoxyacetophenone (DEAP), (1-hydroxycyclohexyl-phenylketone), dibenzoyl disulphide, S-phenyl thiobenzoates, acylphosphine oxide, dibenzoylmethanes, O-acyl α-oximinoketones, phenylazo-4-diphenyl sulphone, benzophenones, flourenones, xanthones, thioxanthones, benzils, ketals (2,2-dimethoxy-2-phenylacetophenone DMP), α-ketocoumarines, anthraquinone, ethyl eosin and terephthalophenones.

Additives

It will be appreciated that one or more additives known in the art of polymer chemistry may be included in the prepolymers, prepolymer compositions or polymers of the invention in amounts up to 20 wt %.

Suitable additives include radical inhibitors to assist in preventing premature polymerisation of a prepolymer or prepolymer composition during storage; sensitisers or promoters to assist in the activation of the cross linking process by accelerating the rate of initiation and/or initiating polymerisation at a desired temperature; other organic additives such as tertiary amines to shift the wavelength at which polymerisation occurs; catalysts; or surfactants.

3,5-di-tert-butyl-4-hydroxytoluene (or 2,6-di-terf-butyl-para-cresol), para-benzoquinone, chloranil, 1,2,3-trihydroxybenzene and 2,4,6-trimethylphenol are examples of radical inhibitors.

Examples of sensitisers include bis-(N,N'-tetraethyl)ethylene diamine, N,N-dimethyl amino ethyl methacrylate, ethyl-4-dimethylaminobenzoate, isopropyl thioxanthone (quantacure ITX), ethyl-p-diaminobenzoate, triethanolamine, tertiary amine (N,N-diethylaminomethacrylate) and Michler's ketone.

The catalyst may be selected from, but is not limited to tin catalysts such as stannous (II) ethylhexanoate, stannous oleate, stannous chloride, dibutyltin dilaurate (DBTDL), dibutylin dioxide, dibutyltin di-2-ethylhexanoate; tertiary amine catalysts such as triethylene diamine, tetramethylbutanediamine (TMBDA), dimethylenthanolamine, 1,8-diazabicyclo [5.4.0]undec-7-ene, 1,4-diazo[2,2,2]dicylcle-octane (DABCO), hydroxy guanine, tetramethyl guanidine, N-ethylmorpholine, riboflavin; titanium catalysts such as titanium ethanol amine, Tyzor-titanate (Tyzor 131), Tyzor organotitanates, titanium butoxide; titanium aqueous chelates which are stable in water such as Tyzor-LA (aqueous titanium lactate chelate), Tyzor 131 (aqueous titanium chelate), Tyzor 217 (aqueous zirconium lactate), Tyzor 218 (aqueous zirconium glycolate); and other catalysts such as calcium phosphate, ovalbumin, sodium acetate and tributyl phosphine.

Curing

The curing/cross linking reaction can be carried out under mild temperature conditions. Typically, the reaction is preferably carried out at temperatures ranging from 20° C. to 40° C.

Variation of the initiator concentrations may control the time frame in which the polymer can be cured into a soft or a hard material and also has an effect on the curing mechanisms.

Variation of each component in the composition may be used to dictate the chemical and physical characteristics of the final cured polymer. For example, lowering the percentage of acrylate groups has the benefit of tailoring the end product to be softer while an increase makes it otherwise. This may be achieved by adding compounds incorporating acrylate groups in excess in the preparation of the prepolymer. Thus, the desired mechanical properties of the materials can be tailored to the application at hand.

Biomedical Uses

The reaction product of the prepolymer or prepolymer composition of the invention and at least one initiator may be used as biodegradable scaffolds for tissue engineering applications such as wound healing, bone, cartilage or nerve repair, cements in dental and periodontal applications, drug delivery and anti adhesive or protective barriers, spinal applications such as spinal disc nucleus replacement. In tissue engineering applications, the prepolymer or prepolymer composition will also contain biological components appropriate to the intended biological use.

It will be appreciated that the scaffold may be either prepared and cured ex vivo and then implanted or its constituent components injected in uncured form for in vivo curing and scaffold preparation.

DETAILED DESCRIPTION OF THE DRAWINGS

In the Examples, reference will be made to the accompanying drawings in which.

EXAMPLES

Figure 1:
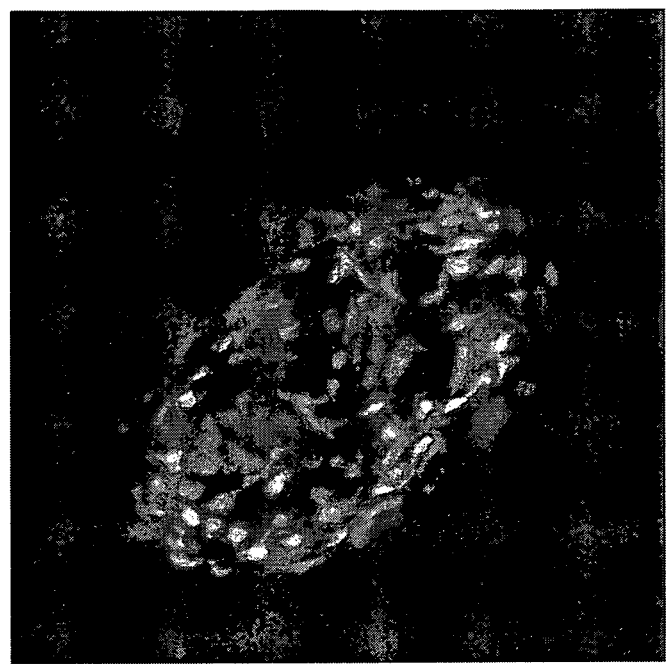
FIG. 1 is a photograph showing chondrocytes on Cultispher-S beads mixed with uncured polymer and left in contact at room temperature for 1 hr as described in Example 4. Viable cells are seen as white areas.
Figure 2:
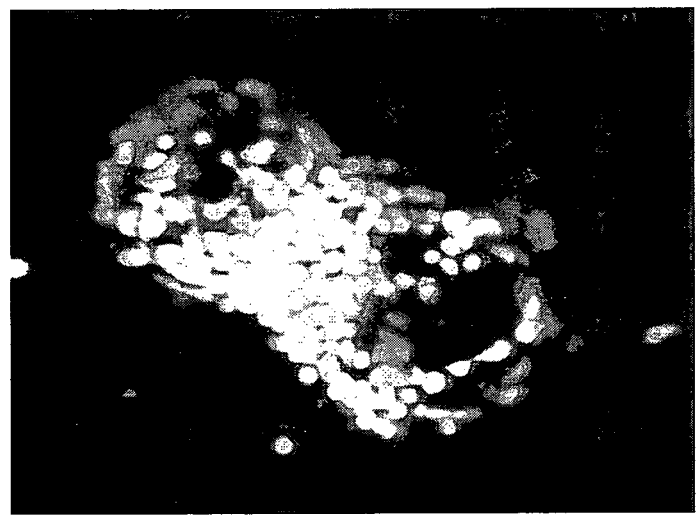
FIG. 2 is a photograph showing chondrocytes on Cultispher-S beads inside a cured polymer plug after 1 hr as described in Example 5. Viable cells are seen as white areas.
Figure 3:
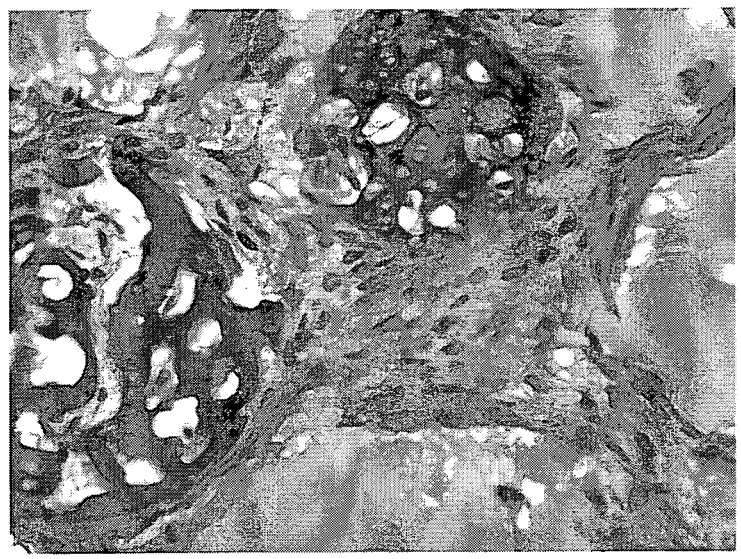
FIG. 3 is a photograph showing chondrocytes growing in and around the Cultispher-S beads and embedded within a cured plug of polymer, the chondrocytes are proliferating as described in Example 5. 8 weeks in cell culture (H&E).
Figure 4:
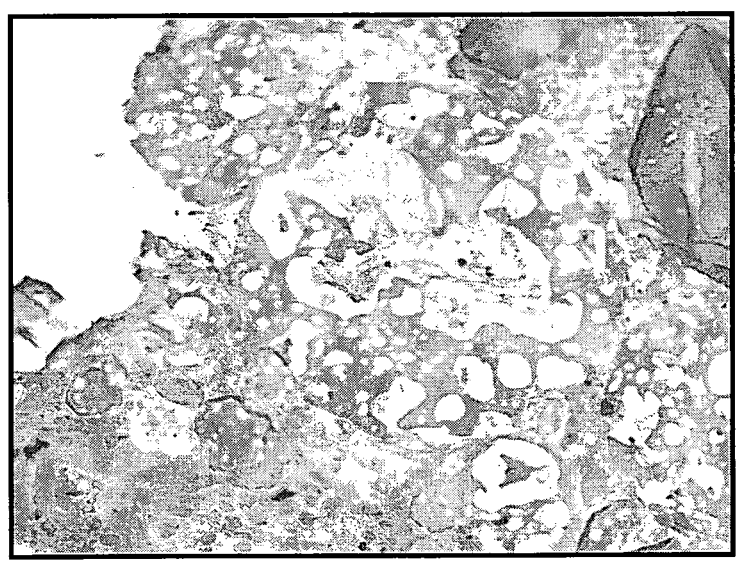
FIG. 4 is a photograph showing chondrocytes after 8 weeks in cell culture producing abundant collagen type II material, shown by the dark-grey staining as described in Example 5.
Figure 5:
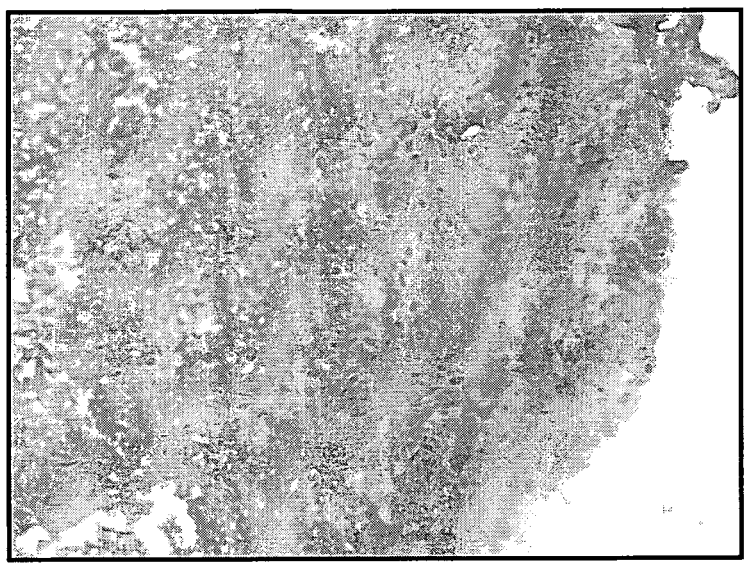
FIG. 5 is a photograph showing chondrocytes after 8 weeks in cell culture producing abundant keratan sulphate material, shown by the dark-grey staining as described in Example 5.
Figure 6:
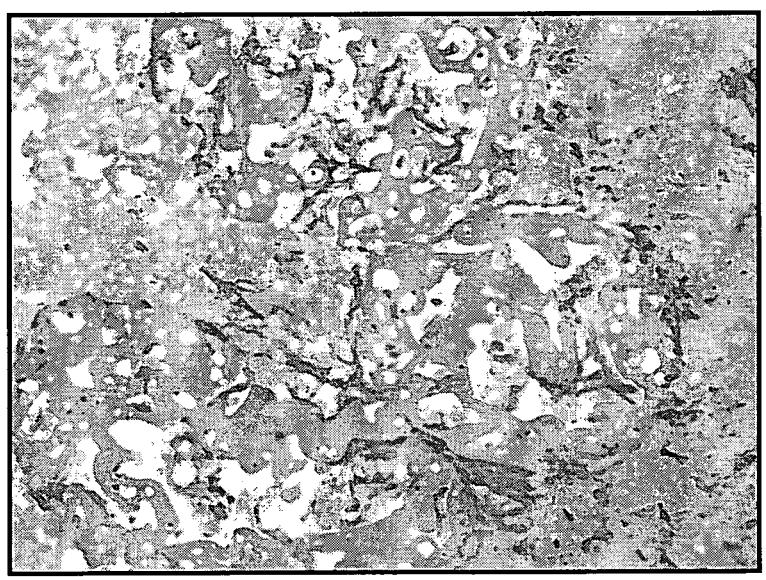
FIG. 6 is a photograph showing chondrocytes after 8 weeks in cell culture producing abundant collagen type VI material, shown by the dark-grey staining as described in Example 5.

The present invention will now be described with reference to the following non-limiting examples.

Example 1

Materials

Polyethylene glycol (PEG) Mn~1500, polycaprolactone triol Mn 900, stannous 2-ethylhexanoate and 3,5-di-tert-butyl-4-hydroxytoluene (BHT) were purchased from Aldrich and used as received. 2-isocyanatoethyl methacrylate (IEM) was purchased from Showa Denko and purified by distilled under reduced pressure. Ethyl lysine diisocyanate (ELDI) was purchased from Kyowa Hakko Kogyo and purified by distilled under reduced pressure.

Methods

Preparation of Acrylate Functionalised Hydrophobic Polyol from Poly(Caprolactone) Triol:

Polycaprolactone triol (Aldrich) (59.17 g, 63.3 mmol) was placed in a round bottom flask and dried at 80° C. in vacuo (0.1 mmHg) for 1 hour. Radical inhibitor BHT (0.1 wt % of total weight, 78.8 mg) and 2-isocyanatoethyl methacrylate (19.65 g, 126.6 mmol) were added to the polyol and stirred at 80° C. Stannous 2-ethylhexanoate catalyst (0.1 wt % of the polyol, 59.2 mg) was then added to the mixture and the reaction was continued stirring overnight. The completion of the reaction was monitored by IR spectroscopy for the disappearance of the isocyanate peak at 2272 $cm^{-1}$. The polyol was characterised by GPC. The hydroxyl and acid numbers were determined according literature reported methods (2). The hydroxyl number was 47.86 and the acid number was 1.23. The number average molecular weight was 1767 and the polydispersity was 1.32 (relative to polystyrene standards).

Preparation of Hydrophilic Prepolymer:

Polyethylene glycol (102.87 g, 61.2 mmol) was placed in a round bottom flask and dried at 80° C. in vacuo (0.1 mmHg) for 1 hour. ELDI (27.69 g, 122.5 mmol) was then added to the polyol and the reaction was stirred overnight at 80° C. The isocyanate content was 3.70% as determined according to ASTM D 5155-01 (3).

Synthesis of Prepolymer Combining Hydrophobic and Hydrophilic Polyols (PCL-PEG)-acrylate (III):

The acrylate functionalised 3-arm polycaprolactone (28.60 g, 26.3 mmol) was placed in a round bottom flask and dried at 80° C. in vacuo (0.1 mmHg) for 1 hour. The reaction was assisted with an overhead mechanical stirrer equipped with a Teflon stirrer blade, and stirred at 80° C. Radical inhibitor BHT (0.1 wt % of the total weight, 33.65 mg) and hydrophilic prepolymer (33.65 g, 13.2 mmol) were added in that order. The reaction was stirred overnight at 80° C. The completion of the reaction was monitored by IR spectroscopy for the disappearance of the isocyanate peak at 2272 $cm^1$. The final polymer was characterised by GPC and the number molecular weight was 5807.

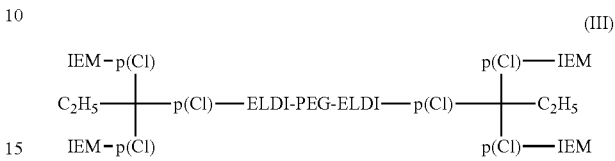

(III)

Example 2

Materials

Polyethylene glycol (PEG) (Mn 1500), stannous 2-ethylhexanoate, p-toluenesulfonic acid monohydrate 85% and 3,5-di-tert-butyl-4-hydroxytoluene (BHT) were purchased from Aldrich and used as received. L-Lactic acid, 88% solution was purchased from DuPont and used as received. Pentaerythritol 98% (Aldrich) was ground then dried at 80° C. overnight before using. ε-caprolactone 99% (Aldrich) was purified by distilled under reduced pressure and stored over 4 Å molecular sieves. 2-isocyanatoethyl methacrylate (IEM) was purchased from Showa Denko and purified by distilled under reduced pressure. Ethyl lysine diisocyanate (ELDI) was purchased from Kyowa Hakko Kogyo and purified by distillation under reduced pressure.

Synthesis of L-lactic Acid-co Caprolactone Polyol:

P(L-LaCl)(IV): Pentaerythritol (16.32 g, 120 mmol) was placed in a 500 mL flask fitted with a magnetic stirrer bar and a reflux condenser. Water (163 mL) was added and the flask was refluxed at 50° C. until the pentaerythritol was completely dissolved. L-lactic acid (20.18 g, 197 mmol) and ε-caprolactone (89.4 g, 784 mmol) were weighed directly into the flask. P-toluenesulphonic acid (0.84 g) and 200 mL of toluene were then added to the mixture. A Dean-Stark apparatus, a reflux condenser and a drying tube were attached to the flask. An additional 150 mL of toluene was placed in the Dean-Stark and the mixture was refluxed at 160° C. As the reaction proceeded, the water collected at the bottom was removed; 63 mL of water was removed and 63 mL of toluene was added to the flask to maintain the same level of the reaction mixture. The reaction was refluxed for approximately 72 h. The polyol was characterized by GPC and NMR. Hydroxyl and acid numbers were determined according to literature[1]. The hydroxyl number was determined to be 177 and the acid number was 0.96. GPC analysis of the product showed number average molecular weight of 1677 and the polydispersity was 1.56 (relative to polystyrene standards).

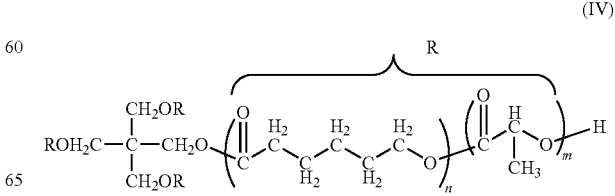

(IV)

Acrylate functionalisation of L-lactic acid-co caprolactone polyol:

P(L-LaCl) polyol (70.04 g, 55.6 mmol) was placed in a flask and dried at 80° C. in vacuo (0.1 mmHg) for 1 hour. Radical inhibitor BHT (0.1 wt % of total weight, 96 mg) and 2-isocyanatoethyl methacrylate (25.87 g, 166.8 mmol) were added to the polyol. Stannous 2-ethylhexanoate catalyst (0.1 wt % of the polyol, 70 mg) was then added to the mixture and the reaction was stirred overnight at 80° C. The completion of the reaction was monitored by IR spectroscopy to the disappearance of the isocyanate peak at 2272 cm$^{-1}$. The hydroxyl and acid numbers were determined according to the method reported in the literature[3]. The hydroxyl number of the polyol was 43.55 and the acid number was 0.90.

Synthesis of Hydrophilic Prepolymer:

Polyethylene glycol (102.87 g, 61.2 mmol, MW (1500)) was placed in a round bottom flask and dried at 80° C. in vacuo (0.1 mmHg) for 1 hour. ELDI (27.69 g, 122.5 mmol) was added to the polyol and the reaction mixture was stirred overnight at 80° C. The isocyanate content of the prepolymer was 3.04% as determined according to ASTM D 5155-01[3].

Synthesis of Prepolymer Combining Hydrophobic and Hydrophilic Compositions [P(L-LaclPeg)-acrylate](IV):

The acrylate functionalised 4-arm P(L-LaCl) (15.50 g, 12.4 mmol) was placed in a round bottom flask and dried at 80° C. in vacuo (0.1 mmHg) for 1 hour. The reaction was assisted with an overhead mechanical stirrer equipped with a Teflon stirrer blade, and stirring at 80° C. Radical inhibitor BHT (0.1 wt % of the total weight, 31 mg) and hydrophilic prepolymer (15.55 g, 6.2 mmol) were added in that order. The reaction was stirred overnight at 80° C. The completion of the reaction was monitor by IR spectroscopy for the disappearance of the isocyanate peak at 2272 cm$^{-1}$. The final prepolymer was characterised by GPC and the number average molecular weight was 5996.

Preparation of 4-arm P(Cl) (V)(MW 900):

Pentaerythritol (15.1 g, 111 mmol), ε-caprolactone (84.82 g, 744 mmol) and stannous 2-ethylhexanoate (0.1 wt % of polyol, 75 mg) were placed in a dry 500 mL flask with a magnetic stirrer bar; the system was kept under inert gas. The reaction flask was heated at 140° C. for 24 hours. The polyol obtained was characterised by GPC and NMR. The hydroxyl and acid numbers were determined according to literature[3] reported methods. The hydroxyl number was 204.4 and the acid number was 2.06. The number average molecular weight was 1257 and the polydispersity was 1.25 (relative to polystyrene standards).

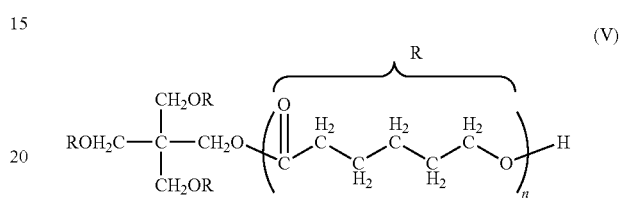

Preparation of Acrylate Functionalised 4-arm Poly(Caprolactone):

Polycaprolactone tetrol (41.20 g, 37.6 mmol) was placed in a round bottom flask and dried at 80° C. in vacuo (0.1 mmHg) for 1 hour. Radical inhibitor BHT (0.1 wt % of total weight, 59 mg) and 2-isocyanatoethyl methacrylate (17.48 g, 115.7 mmol) were added to the polyol. Stannous 2-ethylhexanoate catalyst (0.1 wt % of the polyol, 10 mg) was then added to the mixture and reaction was stirred overnight at 80° C. The completion of the reaction was monitor by IR spectroscopy for the disappearance of the isocyanate peak at 2272 cm-$^{1}$. The polymer obtained was characterised by GPC. The

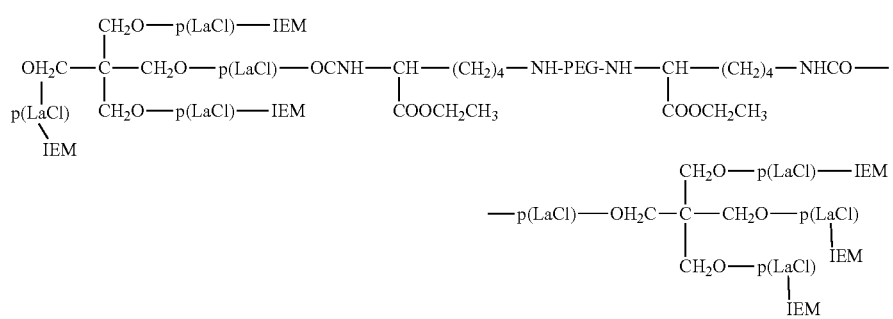

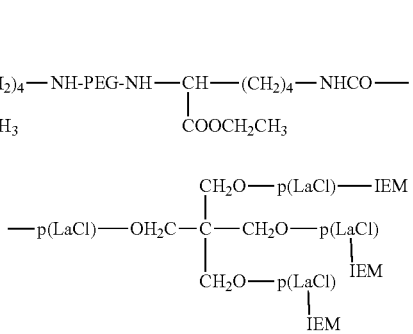

Example 3

Materials

Polyethylene glycol (PEG) Mn~1500, stannous 2-ethylhexanoate, p-toluenesulfonic acid monohydrate 85% and 3,5-di-tert-butyl-4-hydroxytoluene (BHT) were purchased from Aldrich and used as received. L-Lactic acid, 88% solution was purchased from DuPont and used as received. Pentaerythritol 98% (Aldrich) was ground then dried at 80° C. overnight before use. ε-caprolactone 99% (Aldrich) was purified by distilled under reduced pressure and stored over 4A molecular sieves. 2-isocyanatoethyl methacrylate (IEM) was purchased from Showa Denko and purified by distilled under reduced pressure. Ethyl lysine diisocyanate (ELDI) was purchased from Kyowa Hakko Kogyo and purified by distilled under reduced pressure.

hydroxyl and acid numbers were determined according to literature reported methods[3]. The hydroxyl number was 60.94 and the acid number was 1.58. The number average molecular weight was 1775.

Preparation of Hydrophilic Prepolymer:

Polyethylene glycol (102.87 g, 61.2 mmol) was placed in a round bottom flask and dried at 80° C. in vacuo (0.1 mmHg) for 1 hour. ELDI (27.69 g, 122.5 mmol) was then added to the polyol and the reaction mixture was stirred overnight at 80° C. The isocyanate content was 3.43% as determined according to ASTM D 5155-01[3].

Synthesis of Prepolymer Combining Hydrophobic and Hydrophilic Polyols (PCL-PEG)-acrylate:

The functionalised 4-arm polycaprolactone (8.27, 9 mmol) was placed in a round bottom flask and dried at 80° C. in vacuo (0.1 mmHg) for 1 hour. The reaction was assisted with an overhead mechanical stirrer equipped with a Teflon stirrer blade, stirred at 80° C. Radical inhibitor BHT (0.1 wt % of the total weight, 11 mg) and hydrophilic prepolymer (11.03 g, 4.5 mmol) were added in that order. The reaction was stirred overnight at 80° C. The completion of the reaction was monitor by IR spectroscopy for the disappearance of the isocyanate peak at 2272 cm-¹. The final polymer was characterised by GPC and the number average molecular weight was 7508.

as above was weighed into a sterile 4-well cell culture dish (In-vitro Technologies 176740). 0.10 ml of well-settled cells on beads was added from the Nichiryo syringe and gently folded into the polymer with a sterile spatula.

Examination of Uncured Mix

The samples were examined at 15 mins and 1 hr (as shown in FIG. 1) at RT. A sample was taken at the 1 hr and placed into a 10 ml tube. This was then washed 3× in 8 mls of warm PBS, (VI)

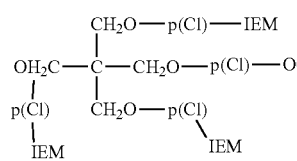 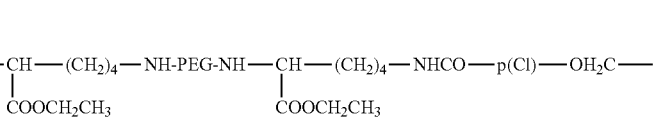 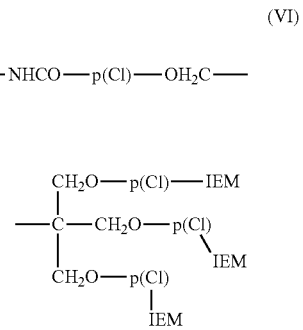

Example 4

This example illustrates that human chondrocytes can be incorporated into the biodegradable, biocompatible compositions of the invention and left in contact with the polymer in an uncured state without compromising cell viability.

Polymer Hydration 0.67 g of prepolymer (III), prepared according to Example 1, was placed in a 25 ml Schott bottle (no. 2) wrapped in foil and sterilised by autoclaving at 121° C. for 15 mins in a small Atherton Autoclave (S/No. 850451117004) then hydrated overnight in dark at room temperature with 20 ml of sterile PBS (phosphate buffered saline).

20 ml sterile PBS changes were then performed on days 1, 2, 5, 6, and 7. The polymer was then left to sit in dark at room temperature, on Day 30 (86.9% hydrated) a sample was taken and used. On Day 70 (88.8% hydrated, a sample was washed with 20 ml sterile PBS just prior to use.

Chondrocyte Preparation

Isolated chondrocytes were seeded from frozen stored samples at a seeding density of $0.75 \times 10^6$ on Cultispher-S beads (Sigma M9043-10G) in Complete Chondrocyte Media (10% FBS in F12:DMEM 1:1). The beads were prepared according to the manufacturers instructions. Briefly, Cultispher-S beads are hydrated at 20 mg/ml in PBS, autoclaved at 121° C. for 15 mins, cooled and stored at 4° C. These cells are grown in and on the Cultispher-S beads, the beads are prewashed with 50 ml of warmed media (DMEM/10% FBS or autologous serum containing 100 µg/ml penicillin and streptomycin) at 37° C. then placed inside a 125 ml spinner bottle. 1.8 mls of the resuspended 20 mg/ml bead solution was used per $0.75 \times 10^6$ chondrocytes. The bottle was then stirred in a 37° C. incubator (with 5% $CO_2$), at 25 rpm intermittently for 2 minutes every 30 minutes for 3 hours, then 45 rpm intermittently for 2 minutes every 30 minutes for the next 3 hours, then continuously at 45 rpm. The chondrocytes were used between 7 and 21 days after this seeding procedure. An aliquot of the chondrocytes on beads are removed from the spinner bottle to a 10 ml tube. The solution was drawn up into a Nichiryo syringe and left for 5 mins in a vertical position for the chondrocytes on beads to settle to the base of the syringe ready for expelling. 0.4 gms of the hydrated polymer prepared the washing was quite vigorous to separate the cells on beads from the surrounding polymer mixture. This mixture was then stained in Molecular Probes Live-Dead Assay Kit L3224 as in the manufacturer's instructions. Briefly 5 mls of PBS at 37 C had added to it 10 µl of solution B (Ethidium Homodimer, stains dead cell nuclei red and is excluded from viable cell nuclei), mixed by vortexing, and 2.5 µl of solution A (Calcein, stains live cell cytoplasm green by interacting with intracellular esterase activity) and vortexed again. 1 ml of stain solution was added to the washed cell/beads, incubated for 20 mins at 37° C. then viewed. Control samples were also prepared in parallel.

Dead control cells were made by taking an aliquot of live cells and adding an excess of 80% ethanol to the cells at room temperature for 10 mins. The cells were then washed in PBS x3 and stained as above. Live cells were taken from the same spinner bottle as the cells for the polymer plug mix, washed and stained as described. The results were viewed using an Optiscan F900e confocal KrAr laser with an Olympus BX61 scope.

Example 5

This example illustrates that human chondrocytes can be incorporated into the biodegradable, biocompatible compositions of the invention and cured to form a solid porous scaffolds without compromising cell viability. In addition cell culture of these plugs show that chondrocytes form new tissue matrix over 8 weeks.

Chondrocyte Preparation

Human articular chondrocytes ($0.75 \times 10^6$ cells, Day 0 post isolation, purchased from Edward Keller, E K 23-7-02, KN8823) were thawed and cultured on Cultispher-S beads as in example 4. The cells were again collected after a further 18 days, counted and the $10 \times 10^6$ cells obtained were seeded onto 0.36 mls of 20 mg/ml Cultispher-S beads to give a final seeded (cells on beads) volume of 0.14 ml. These cells were then mixed with 0.6 mls of polymer (preparation details to follow) to give the final construct. This gave a final cell density of $14.1 \times 10^6$ cells per ml of final formulation of synthetic polymer mixture.

Polymer was prepared as in example 1 and hydrated using the procedure in Example 4. 0.833 g of this hydrated polymer had 0.933 µl of a 1:5 w/w CQ:DMAEMA (camphorquinone and N,N,-dimethyamino ethyl methacrylate) mixed in by sterile spatula. 0.6 g of this polymer mixture was weighed into a sterile tissue culture well. 0.14 ml of the cells on beads mixture was added via Nichiryo syringe and gently folded into the hydrated polymer together the cells/beads/polymer had a final volume of 0.75 mls.

Three plugs were formed in a sterile silicon mould each 140 µl (17.5×5×1.5 mm) and cured with blue light (5×20 s) each using an Elipar™ Free Light 2 (3M ESPE).

Examination of Cured Mix

Cell viability was assessed by use of a LIVE/DEAD viability/cytotoxicity kit, by taking a series of very thin (1 mm) slices from the central region of 1 plug, as described in example 4.

After curing, constructs were either left whole or cut in half. The remaining plugs were either cultured in 6 well suspension plates (static) or in dynamic motion (spinner). Cultures were grown in the presence of long term ascorbic acid, at a final concentration of 28.9 µg/ml. A 10 mM stock stored at 4° C. was used at a 1 in 100 dilution. (Wako L-ascorbic acid phosphate Mg salt, Novachem cat No. 013-12061). Media was changed twice weekly for a period of 8 weeks.

The plug pieces were then cut in half and either fixed with 10% neutral buffered formalin and processed for standard histology and stained with Haematoxylin and Eosin, or snap frozen in liquid nitrogen cooled isopentane. These frozen plugs were then stained with antibodies directed against collagen type II, keratan sulphate and type VI collagen. The results are shown in FIGS. 2 to 6.

Example 6

This example shows that the polymer may be hydrated by a different method to that used in Example 4.

The polymer prepared according to the procedure of Example 1 was hydrated using a daily wash method and shown to be biocompatible with chondrocytes in both the 1 hr uncured test and cured 8-week cell culture.

Polymer Hydration 0.5 gm aliquots of polymer of Example 1 were weighed into bottles and autoclaved as in Example 4. 20 mls of sterile PBS solution was added and then removed and changed on a daily basis for 12 days. The PBS was removed and 0.4 gm of this hydrated polymer weighed into a sterile 4-well cell culture dish (Invitro Technologies 176740) 0.10 ml of well-settled cells on beads was added, as prepared in Example 4, from the Nichiryo syringe and gently folded into the polymer with a sterile spatula as in Example 4.

Figure 7:
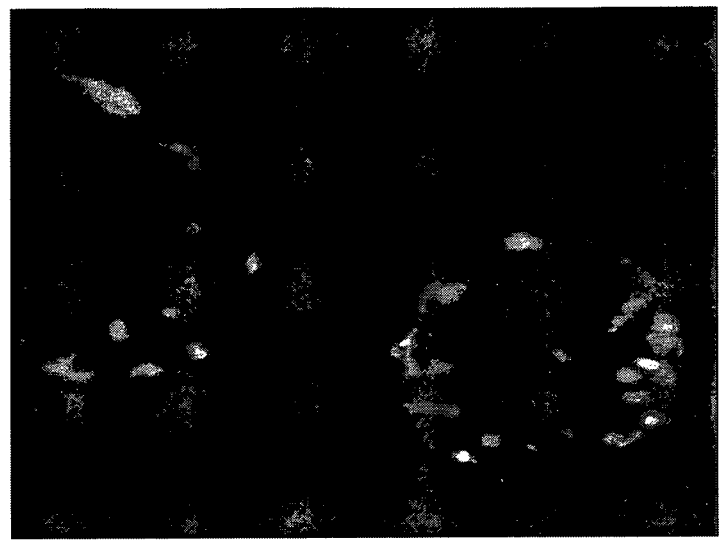
FIG. 7 is a photograph showing chondrocytes on Cultispher-S beads mixed with uncured polymer and left in contact at RT for 1 hr as described in Example 6.
Figure 8:
FIG. 8 is a photograph showing culture of chondrocytes on beads within polymer scaffolds cured and examined after 1 hr as described in Example 6. Viable cells are seen as white areas.
Figure 9:
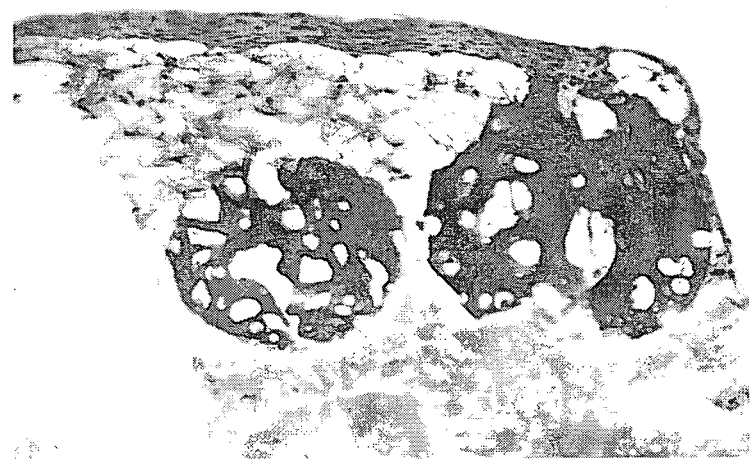
FIG. 9 is a photograph showing chondrocytes growing in and around the Cultispher-S beads and embedded within a cured plug of polymer, the chondrocytes are proliferating as described in Example 6.8 weeks in cell culture (H&E).
Figure 10:
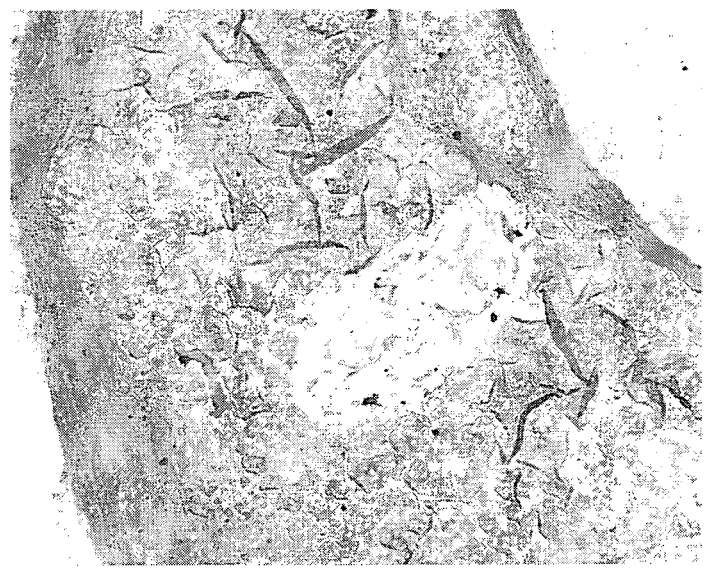
FIG. 10 is a photograph showing chondrocytes after 8 weeks in cell culture producing abundant collagen type II material, shown by the dark-grey staining as described in Example 6.
Figure 11:
FIG. 11 is a photograph showing chondrocytes after 8 weeks in cell culture producing abundant keratan sulphate material, shown by the dark-grey staining as described in Example 6.
Figure 12:
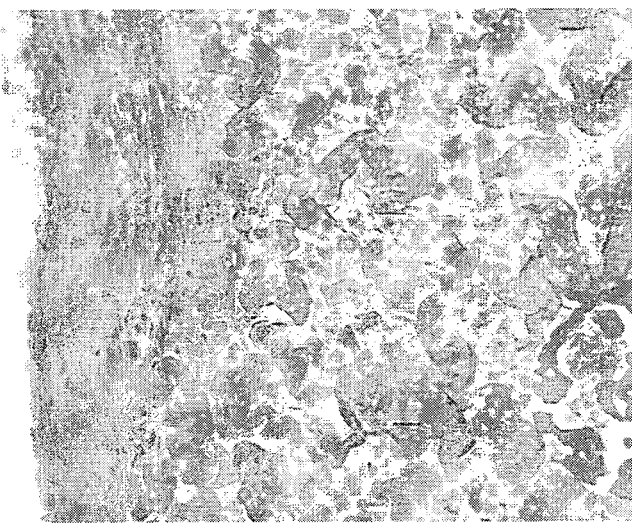
FIG. 12 is a photograph showing chondrocytes after 8 weeks in cell culture producing abundant collagen type VI material, shown by the dark-grey staining as described in Example 6.

This material was examined in 3 ways.
1. Chondrocytes on beads in contact with the uncured polymer for 1 hr at RT (see FIG. 7).
2. Culture of chondrocytes on beads within polymer scaffolds cured and examined after 1 hr (see FIG. 8).
3. Culture of chondrocytes on beads within polymer scaffolds cured and grown in cell culture for 8 weeks (see FIGS. 9 to 12).

Example 7

Polymer prepared according to the procedure described in Example 1 was hydrated using an enhanced saturation process method (ESP) and shown to be biocompatible with chondrocytes in the 1 hr uncured test.

Polymer Hydration 1.5 gram aliquot in a straight sided glass vial (approx 20 ml capacity) of the polymer had 15.0 g of PBS added to it. This was hand-mixed with a spatula for 3 minutes before the high speed mixing. The mixer (Ika-Werke Ultra Turrax T8) was used for 5 mins at RT on speed 4, which gave a frothy dispersion. The bottle was then centrifuged for 5 mins @2000 rpm in a Beckman Coulter Allegra X-12R centrifuge and afterwards, the excess PBS was removed and the % hydration calculated at 83.4%.

Figure 13:
FIG. 13 is a photograph showing chondrocytes on Cultispher-S beads mixed with uncured polymer, made with the ESP hydration method and left in contact at RT for 1 hr as described in Example 7. Viable cells are seen as white areas.

Chondrocytes were prepared for addition to this mix as in Example 4, and the experimental procedure for analysing the sample was also as for Example 4. Briefly 0.4 gm of the enhanced saturation process material was combined with 0.1 ml of chondrocytes as in Example 4 and the results are shown in FIG. 13.

References
1. [Volgaris D, Tsitsilianis C, Grayer V, Esselink F J, Hadzioannou G. Polymer 1999; 405879-89)
2. Strategy for Cell Therapy: Polymers for Live Cell Encapsulation and Delivery, Satya Prakash and Hahn Soe-Lin in Trends Biomater. Artif. Organs Vol 18 (1), pp 24-35 (2004)
3. N-Methylimidazole as a Catalyst for Acetylation of Hydroxyl Terminated Polymers by Louis A. Dee and others. Analytical Chemistry, 1980, 52, 572-573.
4. ASTM D 2849-69. (Sections 31 to 39) Standard Methods of Testing URETHANE FOAM POLYOL RAW MATERIALS. Method A—Acetic Anhydride Pressure Bottle section.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be understood to persons skilled in the art of the invention that many modifications may be made without departing from the spirit and scope of the invention.

The invention claimed is:

1. A biocompatible, biodegradable prepolymer composition comprising: hydrophilic prepolymers and hydrophobic prepolymers, wherein at least one of the hydrophobic prepolymers has at least one ethylenically unsaturated functional group and at least 5% of the total number of hydrophilic and hydrophobic prepolymers have two or more ethylenically unsaturated functional groups; and water;

wherein the hydrophilic prepolymers are prepared from a polyethylene glycol, polypropylene glycol, polyvinyl alcohol, polythiols based on butanedithiol, hexanedithiol or pentaerythritol tetrakis (3-mercaptopropionate), copolymers of said polythiols, polyacrylamides, polyvinyl pyrolidone, polyhydroxyethyl methacrylate or block, graft or random copolymers thereof; and wherein the hydrophobic prepolymers are prepared from di or higher hydroxyl or amine functionalized oligomers based on esters, carbonates, anhydrides, orthoesters, lactones, phosphazenes.

2. The biocompatible, biodegradable prepolymer composition of claim 1 wherein at least 25% of the total number of hydrophilic and hydrophobic prepolymers have two or more ethylenically unsaturated functional groups.

3. The biocompatible, biodegradable prepolymer composition of claim 1 wherein at least 40% of the total number of hydrophilic and hydrophobic prepolymers have two or more ethylenically unsaturated functional groups.

4. The biocompatible, biodegradable prepolymer composition of claim 1 wherein the hydrophilic prepolymers contain at least one functional group selected from the group consisting of thiol or hydroxyl and the hydrophobic prepolymers contain at least one functional group selected from the group consisting of hydroxyl, or amine.

5. The biocompatible, biodegradable prepolymer composition of claim 1 wherein the hydrophilic prepolymers or hydrophobic prepolymers contain at least one urethane/urea linkage formed by reaction of isocyanate with polyethylene glycol, polypropylene glycol, polyvinyl alcohol, polythiols based on butanedithiol, hexanedithiol or pentaerythritol tetrakis (3-mercaptopropionate), copolymers of said polythiols, polyacrylamides, polyvinyl pyrolidone, polyhydroxyethyl methacrylate or block, graft or random copolymers thereof or formed by reaction of isocyanate with di or higher hydroxyl or amine functionalized oligomers based on esters, carbonates, anhydrides, orthoesters, lactones, phosphazenes.

6. The biocompatible, biodegradable prepolymer composition of claim 1 which is soluble, miscible or forms an emulsion or paste when mixed with additional water.

7. A biocompatible, biodegradable polymer composition which is the reaction product of: hydrophilic prepolymers and hydrophobic prepolymers, wherein at least one hydrophobic prepolymer has at least one ethylenically unsaturated functional group and at least 5% of the total number of hydrophilic and hydrophobic prepolymers have two or more ethylenically unsaturated functional groups; and water;
  wherein the hydrophilic prepolymers are prepared from polyethylene glycol, polypropylene glycol, polyvinyl alcohol, polythiols based on butanedithiol, hexanedithiol or pentaerythritol tetrakis (3-mercaptopropionate) or copolymers of said polythiols thereof, polyacrylamides, polyvinyl pyrolidone and polyhydroxyethyl methacrylate or block, graft or random copolymers thereof; and
  wherein the hydrophobic prepolymers are prepared from di or higher hydroxyl or amine functionalized oligomers based on esters, carbonates, anhydrides, orthoesters, lactones, phosphazenes.

8. The biocompatible, biodegradable polymer composition of claim 7 wherein at least 25% of the total number of hydrophilic and hydrophobic prepolymers have two or more ethylenically unsaturated functional groups.

9. The biocompatible, biodegradable polymer composition of claim 7 wherein at least 40% of the total number of hydrophilic and hydrophobic prepolymers have two or more ethylenically unsaturated functional groups.

10. The biocompatible, biodegradable polymer composition of claim 7 wherein the hydrophilic prepolymers contain at least one functional group selected from the group consisting of thiol or carboxyl and the hydrophobic prepolymers contain at least one functional group selected from the group consisting of hydroxyl, or amine.

11. A cured biocompatible, biodegradable polymer comprising the reaction product of the polymer composition according to claim 7 and at least one initiator.

12. A biocompatible, biodegradable scaffold comprising the reaction product of the polymer composition according to claim 7 and at least one initiator.

13. The biocompatible, biodegradable polymer composition of claim 7 wherein the urethane/urea linkage formed by reaction of isocyanate with polyethylene glycol, polypropylene glycol, polyvinyl alcohol, polythiols based on butanedithiol, hexanedithiol or pentaerythritol tetrakis (3-mercaptopropionate), copolymers of said polythiols, polyacrylamides, polyvinyl pyrolidone, polyhydroxyethyl methacrylate or block, graft or random copolymers thereof or formed by reaction of isocyanate with di or higher hydroxyl or amine functionalized oligomers based on esters, carbonates, anhydrides, orthoesters, lactones, phosphazenes.

14. The biocompatible, biodegradable polymer composition of claim 7 which is soluble, miscible or forms an emulsion or paste when mixed with additional water.

* * * * *